(12) United States Patent
Somberg et al.

(10) Patent No.: US 8,664,267 B2
(45) Date of Patent: Mar. 4, 2014

(54) PARENTERAL SOLUTION CONTAINING AMIODARONE IN NNDMA (N,N,-DIMETHYLACETAMIDE)

(75) Inventors: John Charin Somberg, Lake Forest, IL (US); Vasant V. Ranade, Libertyville, IL (US)

(73) Assignee: Academic Pharmaceuticals Incorporated, Lake Bluff, IL (US)

( * ) Notice: Subject to any disclaimer, the term of this patent is extended or adjusted under 35 U.S.C. 154(b) by 1066 days.

(21) Appl. No.: 11/786,351

(22) Filed: Apr. 12, 2007

(65) Prior Publication Data

US 2008/0255229 A1     Oct. 16, 2008

(51) Int. Cl.
*A61K 31/343*     (2006.01)

(52) U.S. Cl.
USPC .......................................... 514/469; 514/557

(58) Field of Classification Search
USPC .......................................................... 514/183
See application file for complete search history.

(56) References Cited

U.S. PATENT DOCUMENTS

| | | | | |
|---|---|---|---|---|
| 3,639,174 | A * | 2/1972 | Kegelman | 429/339 |
| 5,387,419 | A * | 2/1995 | Levy et al. | 424/422 |
| 2001/0041720 | A1* | 11/2001 | Ankersen | 514/321 |
| 2006/0040896 | A1* | 2/2006 | Kennedy | 514/56 |

* cited by examiner

*Primary Examiner* — Jeffrey S. Lundgren
*Assistant Examiner* — Meghan Finn
(74) *Attorney, Agent, or Firm* — Vance Intellectual Property, PC

(57) ABSTRACT

Disclosed herein are parenteral solutions containing 3-diethylaminoethoxy benzoyl-benzofurans, such as amiodarone, in a diluent NNDMA (N,N-Dimethylacetamide) useful in the treatment of cardiac arrhythmias both supraventricular, ventricular as well as, the condition of cardiac arrest.

18 Claims, 3 Drawing Sheets

Figure 1A:
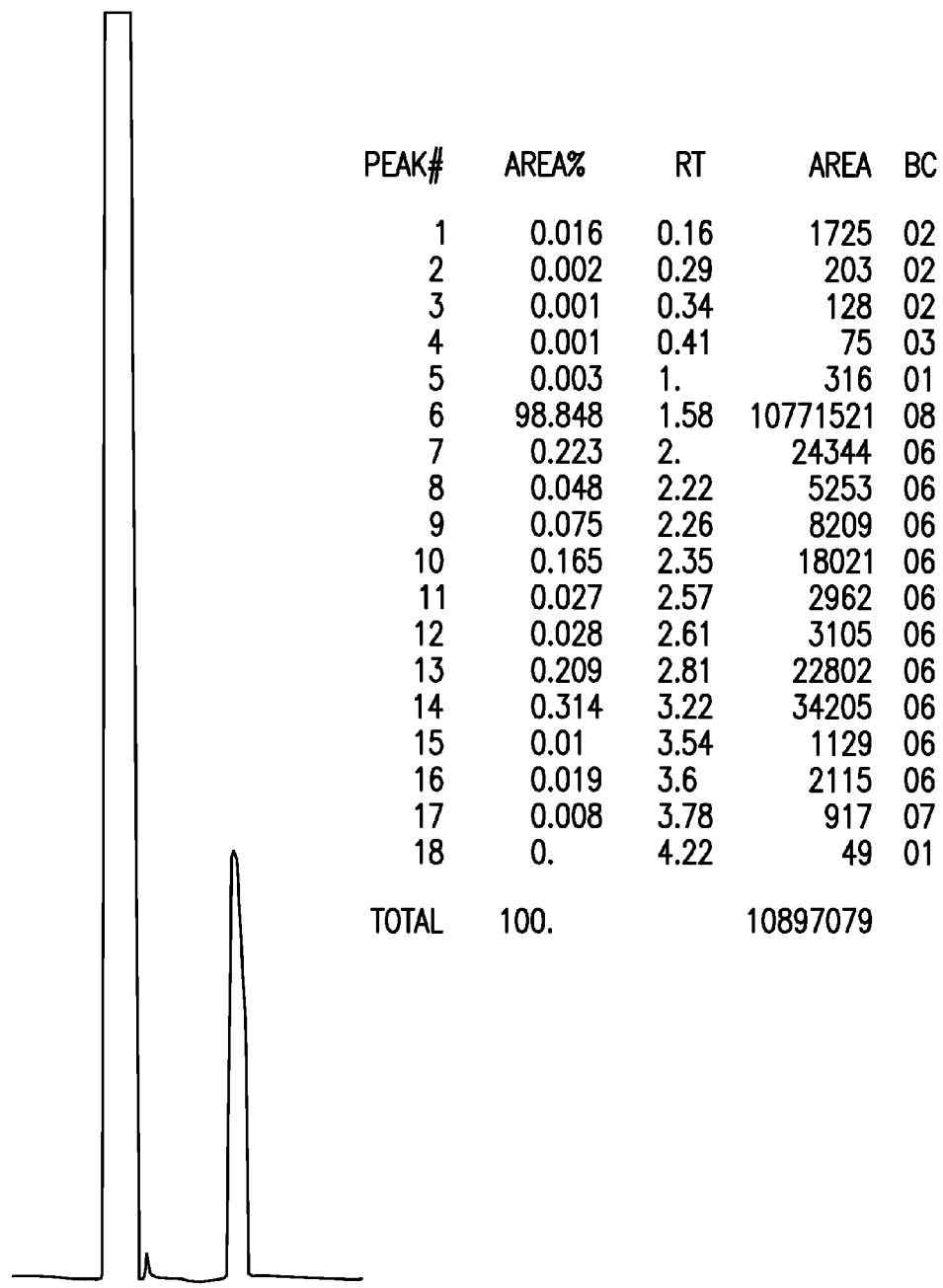

| PEAK# | AREA% | RT | AREA | BC |
|---|---|---|---|---|
| 1 | 0.071 | 0.08 | 7499 | 02 |
| 2 | 0.038 | 0.24 | 4070 | 02 |
| 3 | 0.095 | 0.39 | 10089 | 02 |
| 4 | 0.074 | 0.61 | 7834 | 02 |
| 5 | 0.154 | 0.75 | 16411 | 02 |
| 6 | 0.037 | 1.21 | 3935 | 02 |
| 7 | 0.073 | 1.39 | 7706 | 02 |
| 8 | 99.352 | 1.81 | 10555880 | 08 |
| 9 | 0. | 2.87 | 3 | 05 |
| 10 | 0.005 | 3.03 | 564 | 05 |
| 11 | 0.101 | 3.46 | 10761 | 05 |
| TOTAL | 100. | | 10624752 | |

PARENTERAL SOLUTION CONTAINING AMIODARONE IN NNDMA (N,N,-DIMETHYLACETAMIDE)

BACKGROUND OF THE INVENTION

The present invention relates to novel parenteral solutions containing 3-diethylaminoethoxybenzoylbenzofurans having the following structural formula:

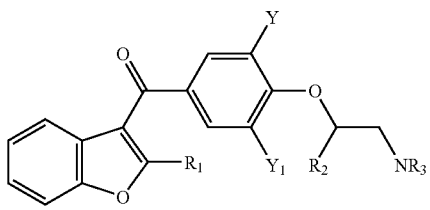

Wherein $R_1$ is alkyl, $R_2$ is hydrogen or methyl, $NR_2$ is hydrogen or methyl, $NR_3$ is dimethylamino, diethylamino, dipropylamino, piperidino, pyrrolidino or morpholino, and Y and $Y_1$ are hydrogen, iodo- or bromo-. More particularly, the present invention relates to a parenteral solution suitable for intravenous administration containing as active ingredient 2-n-butyl-3-(3,5-diiodo-4-β-N-diethylaminoethoxy-benzoyl)benzofuran (hereinafter amiodarone).

Amiodarone has been approved in an oral tablet form (Cordarone®) for the treatment of life-threatening ventricular tachyarrhythmias in the United States since 1985. This drug is useful not only in treating these arrhythmias but also in treating less severe ventricular arrhythmias and many supraventricular arrhythmias including atrial fibrillation and reentrant tachyarrhythmias involving accessory pathways.

To treat arrhythmias, the compound may be administered in oral dosage forms such as in the form of a 200 mg tablet, or it may be administered in the form of an intravenous solution. Please see, for example, Escoubet, B. et al., "Suppression of Arrhythmias Within Hours After Single Oral Dose of Amiodarone and Relation to Plasma and Myocardial Concentrations", *Am. J. Cardiol.*, (1985), 55:696-702, Mostow et al., "Rapid Suppression of Complex Ventricular Arrhythmias With High-Dose Oral Amiodarone", *Circulation*, (1986), 73:1231-8, Morady et al., "Intravenous Amiodarone in the Acute Treatment of Recurrent symptomatic Ventricular Tachycardia", *Am. J. Cardiol.*, (1983), 51:156-9 and Kadish et al. "The Use of Intravenous Amiodarone in the Acute Therapy of Life-Threatening Tachyarrhythmias". *Progress in Cardiovascular Diseases*, (1989), 31:4, 281-294.

Amiodarone is practically insoluble or slightly soluble in an aqueous solvent at very low concentrations. It is difficult to formulate a dosage from suitable for intravenous administration. To aid the dissolution in water, for example, a surfactant has been suggested. Thus, the prior art intravenous dosage form for this compound termed I.V. Cordarone, comprises amiodarone dissolved in a solvent comprising polysorbate 80 available under the tradename Tween-80, and benzyl alcohol. Prior art intravenous solutions of amiodarone will be designated IV Cordarone herein.

However, the use of this dosage form is highly undesirable because it exhibits deleterious cardiovascular effects attributable to the detergent. For example, Torres-Arrault et al. reported in *Journal of Electrocardiology*, 17 (2), 1984, pp 145-152 that Tween-80 is a potent cardiac depressant and causes hypotension in a dog. See also Gough et al., "Hypotensive Action of Commercial Intravenous Amiodarone and Polysorbate 80 in Dogs", *Journal of Cardiovascular Pharmacology*, (1982), 375-380.

Kosinzki, et al., *Am J. Cardiol.*, (1984) 4:565-70 report that intravenous amiodarone (IV Cordarone) can result in significant impairment of left ventricular performance in patients with preexisting left ventricular dysfunction. After acute intravenous bolus administration, patients with a left ventricular ejection fraction greater than 0.35 experienced improved cardiac performance due to both acute and chronic peripheral vasodilation. However, patients with a lower ejection fraction developed a 20% decrease in cardiac index and clinically significant elevation of right heart pressures after acute bolus administration.

Remme et al., *Am Heart J.*, (1991) 122:96-103 report that intravenous amiodarone caused a 15% reduction in blood pressure and an 18% increase in heart rate, and a progressive reduction in contractility ($V_{max}$) with a rise in left ventricular end diastolic pressure.

Bopp et al., *J. Cardio. Pharmacol.*, (1985) 7:286-289 report that IV Cordarone caused a decrease in the ejection fraction, an increase in pulmonary wedge pressure and a 15% decease in dP/dt, and a 12% decrease in left ventricular work.

Each of the above three references discuss the effects of intravenous amiodarone (IV Cordarone), i.e., amiodarone solubilized for intravenous administration using polysorbate 80 and benzyl alcohol. Previously 2-N-butyl-3-(3,5-diiodo-4-β-N-diethylamino-ethoxybenzoyl)benzofuran (amiodarone) was prepared for solubilization using an acetate buffer. In practice amiodarone HCl, which may be purified and crystalline can be dissolved in a buffer system comprising a weak acid and a salt of the weak acid, and more particularly a combination of acetic acid and sodium acetate having a pH below 4.0 and in particular at a range of about 3.5 to 3.8 with a molar concentration of about 0.05 to about 0.1 M. An effective antiarrhythmic amount of amiodarone eg: about 25 to 75 mg/ml is mixed together with buffer and heated to a temperature not to exceed about 75° C. until a solution is complete. This process has the drawback of requiring a heating and cooling stage in the manufacture process and yields an acetic solution that may give rise to a venous phlebitis at the site of intravenous administration.

DESCRIPTION OF THE PRIOR ART

Prior art is replete with the preparation and use of amiodarone. Fore example, U.S. Pat. No. 3,248,401 issued Apr. 26, 1966 describes the preparation of 3-diethylaminoethoxybenzoyl benzofurans the disclosure of which is incorporated herein by reference.

*Physicians' Desk Reference*, 1992, page 2446 under tradename Cordarone®, provides the prescribing information relating to the oral form of this important product.

The Torres-Arrault, Taska and Gough articles described above set forth the hypotensive effects following intravenous administration of IV Cordarone (amiodarone in Tween-80).

The article "Intravenous Amiodarone", *Clinical Progress in Electrophysiology and Pacing*, (1986), 4:5, page 433 concludes that "Amiodarone, when administered intravenously, appears to have a rapid onset of action causing profound hemodynamic and electrophysiological effect".

DESCRIPTION OF PRIOR ART

Gallik et al describes the lack of myocardial depressant effects of an intravenous amiodarone that is devoid of Tween 80 and benzyl alcohol. Galik et al, "Hemodynamic and surface electrocardiographic effects of a new aqueous formulation of intravenous amiodarone" *Am J Cardiol* 2002; 90:964-968.

Somberg et al describes an acetate formulation that shows less toxicity than the amiodarone formulation that contains Tween 80 and benzyl alcohol as diluents. Somberg et al, "Pharmacology and toxicology of a new aqueous formulation of intravenous amiodarone (Amio-Aqueous) compared with Cordarone IV" *Am J Therapeutics* 2005; 12, 9-16.

Somberg et al describes an aqueous amiodarone that is more effective than lidocaine and can be given by IV bolus with less hypotension than that reported with Tween 80 and benzyl alcohol. Somberg et al, "Intravenous lidocaine versus intravenous amiodarone (in a new aqueous formulation) for incessant ventricular tachycardia" *Am J Cardiol* 2002; 90:853-859.

Somberg et al describes the lack of hypotension of a bolus of an aqueous formulation of amiodarone in conscious dogs as contrasted to amiodarone in Tween 80 and benzyl alcohol. Somberg et al, "Comparative effects of rapid bolus administration of aqueous amiodarone versus 10-minute Cordarone IV infusion on mean arterial blood pressure in conscious dogs. *Cardiovascular Drugs and Therapy* 2004; 18:345-351.

Somberg et al reports a lack of hypotensive effect with rapid administration of a new aqueous formulation of intravenous amiodarone. Somberg et al, "Lack of hypotensive effect with rapid administration of a new aqueous formulation of intravenous amiodarone" *Am J Cardiol* 2004; 93:576-581.

SUMMARY OF THE INVENTION

The present invention relates to parenteral solutions comprising as an active ingredient a 3-diethylaminoe-thoxybenzoyl-benzofuran with the following structural formula:

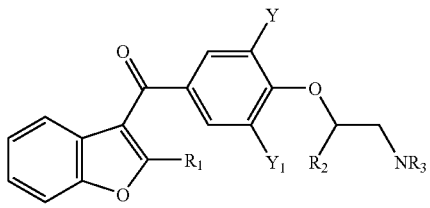

Wherein $R_1$ is alkyl, $R_2$ is hydrogen or methyl, $NR_3$ is dimethylamino, diethylamino, dipropylamino, piperidino, pyrrolidino or morpholino and Y and $Y_1$ are identical and represent hydrogen, iodo or bromo. More particularly, the present invention relates to a parenteral solution suitable for intravenous administration containing as an active ingredient an effective antiarrhythmic amount of 2-N-butyl-3-(3,5-dido-4-β-N-diethylamino-ethoxybenzoyl)benzofuran (amiodarone) in a sterile solvent comprising NNDMA (N,N-Diamethylacetamide) at a concentration ranging from 1 to 50% by volume of the solution.

The present invention also includes within its scope a method for producing such a solution.

Figure 1B:
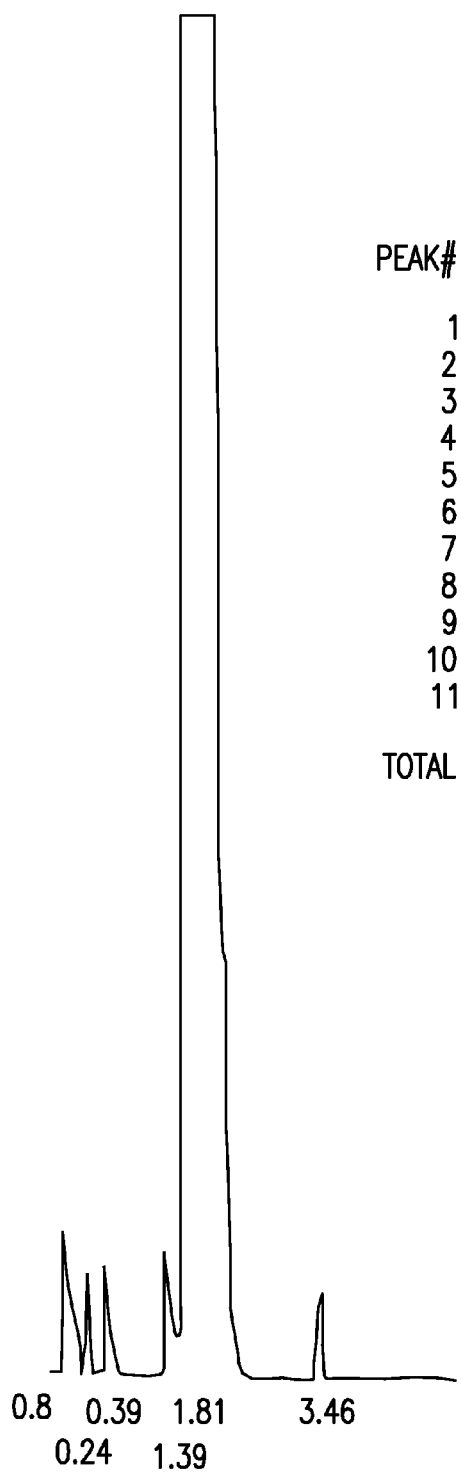

FIGS. 1A and 1B show the results of high performance liquid chromatography (HPLC) performed on a sample of amiodarone in NNDMA (1A) and IV Cordarone (amiodarone in polysorbate-80)(1B). In FIG. 1A, the large peak is the amiodarone peak. In FIG. 1B, the narrow spikes belong to the polysorbate 80 peak and the large peak is the amiodarone peak.

Figure 2:
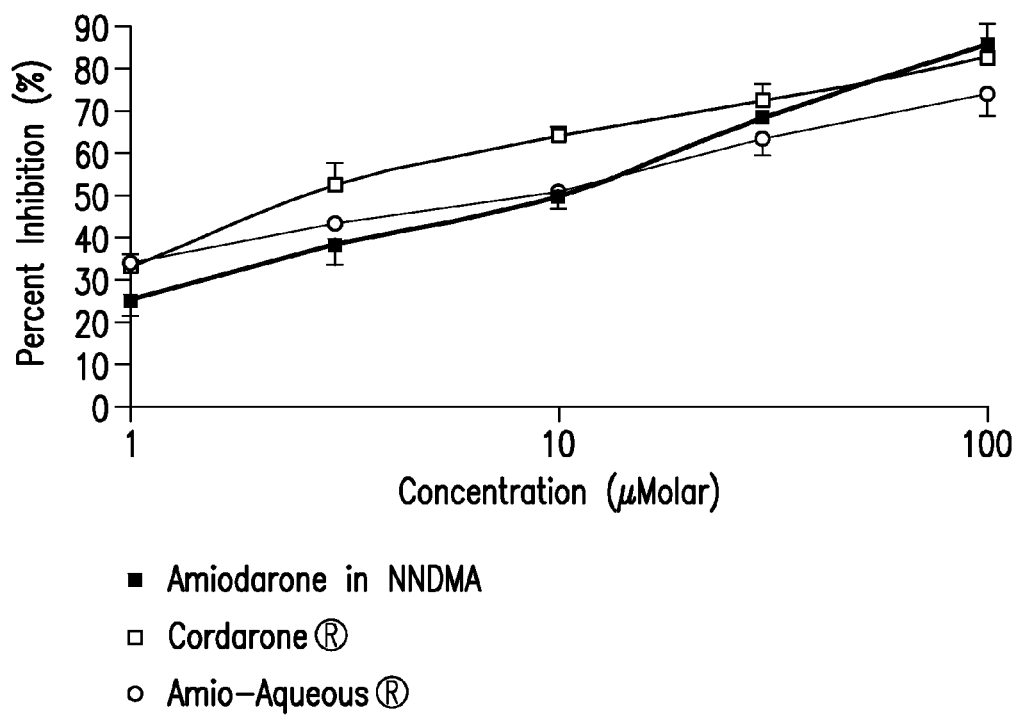

FIG. 2 shows the effect of increasing amiodarone concentration (amiodarone in NNDMA versus amiodarone in benzyl alcohol and Tween 80 or acetate buffer) on % inhibition of potassium current in oocytes with HERG channels overexpressed on the cell membrane. The results show identical activity of the amiodarone preparations.

DETAILED DESCRIPTION OF THE INVENTION

According to the present invention, there is provided parenteral solutions containing as an active ingredient 3-diethylaminoethoxybenzol benzofuran having the following structural formula:

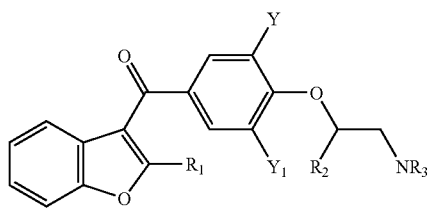

Wherein $R_1$ is alkyl of 1-6 carbon atoms, $R_2$ is hydrogen or methyl and $R_3$ is dimethylamino, diethylamino, dipropylamino, piperidino, pyrrolidino or morpholino, and $Y_1$ and $Y_2$ are hydrogen, iodo or bromo. In particular, the present invention relates to a parenteral solution suitable for intravenous administration comprising as an active ingredient an effective antiarrhythmic amount of a selected substituted benzofuran, i.e., amiodarone in a vehicle which is described more fully below.

In a typical practice of the present invention, amiodarone HCl, which may be purified and crystalline, is dissolved in a buffer system comprising NNDMA, N,N-Dimethylacetamide in a concentration of between 1 and 50% by volume at a pH of between 4.5 and 7.0. An effective antiarrhythmic amount 10 to 100 mg/ml can be mixed together with the amiodarone in sterile water till the material dissolves. Thereafter, the resulting solution is placed in vials or ampules or other containers suitable for dispersing the drug as a parenteral product.

The preparation thus obtained was found, quite surprisingly, to remain in solution, which of course is an important attribute for a product for intravenous administration. In fact, the product shows remarkable stability when stored at room temperature or at 40° C. over a 6 month period without the formation of turbidity, precipitate or degradative products. Formulations of amiodarone were prepared in various solvents containing NNDMA, and glycerol, glucose, Tween 20, 40, 60, 80, 1-propanol, 2-propanediol, PEG 300, 400 and 600. These solutions were not stable and thus surprisingly only the NNDMA diluent (1% in 5% dextrose solution) was effective in keeping amiodarone in solution. Stability of these solutions is reported in table 1.

The solution thus formulated is indicated for the treatment of life threatening, sustained ventricular tachycardia or fibrillation without the fear of the undesirable side effects observed with the administration of a solution of amiodarone in Tween-80 or the potential adversities caused by an acidic solution of amiodarone. As with any potent drug, the dosage must be individualized by the treating clinician.

In order to further illustrate the practices of the invention, the following examples are included.

Example 1

Solubilization of Amiodarone in an Aqueous Solution

The vehicle for dissolving amiodarone consists of NNDMA (N,N-Dimethylacetamide) in 5% dextrose solution, percentage by volume of a range of 1 to 50% with amiodarone added at a concentration of 25 to 100 mg/ml. As an example, to make a 50 mg/ml solution, one ml of NNDMA is added to 48 ml of 5% dextrose solution and 50 mg of amiodarone with water added to complete the volume of 50 ml and pH is adjusted to 5.5-6.0. The material is mixed using a Vortex mixer for 1 to 5 min. till the amiodarone powder is completely dissolved. Amiodarone dissolved in the new vehicle remains in solution at room temperature at a concentration of between 25 and 100 mg/ml for extended periods of time as long as the solution is shielded from light and under a nitrogen or similar inert chemical blanket.

Example 2

Characteristics and Attributes of the Preparation of Example 1

The most important characteristic of the amiodarone acetate buffer preparation is that amiodarone remains in solution. To analyze solution stability, solutions of 25-150 mg/ml, particularly about 50 mg/ml, amiodarone was prepared as described in Example 1 and maintained at room temperature. The solutions at a pH of 6.5 was examined periodically over a period of six months following preparation; the solutions remained perfectly clear, i.e., no sign of turbidity or precipitate.

Evaluation of the amiodarone-acetate buffer solution developed through this process demonstrates that the physical and chemical properties of amiodarone remain unchanged as determined by HPLC. As shown in FIG. 1A and 1B, the peak of amiodarone dissolved in polysorbate 80 (Tween-80) is identical to the peak observed for the amiodarone HCl in the acetate buffer of the present invention (FIG. 1B). The Tween-80 peak of the former preparation is clearly visible, this being the only difference between the two HPLC tracings.

Example 3

Biologic Activity

Antiarrhythmic Activity

The activity of amiodarone that is relevant here is the drug's antiarrhythmic action. A standard method of determining activity is to ligate the left anterior descending coronary artery of the rat and record the arrhythmic activity with and without antiarrhythmic drug pretreatment. The effects of increasing doses of the IV Cordarone was evaluated following coronary occlusions with the administration of the drug intravenously 15 minutes before coronary occlusion. While ventricular premature contraction (VPC) frequency was only suppressed at the highest doses, the frequency and severity of the most serious arrhythmias, ventricular tachycardia (VT) and ventricular fibrillation (VF) are suppressed in a dose dependent fashion (Table 2). Amiodarone prepared according to Example 1 studied at the same range of doses caused a decrease in VPC frequency, as well as VT and VF incidence (Table 3). This dose-dependent suppression of arrhythmias seen with amiodarone is significantly different than that seen with the saline control group. The amiodarone-acetate buffer preparation (maintained at room temperature for two months) was equally effective as that of a freshly prepared solution. Thus the preparation of the present invention demonstrated long term biologic stability.

TABLE 2

Antiarrhythmic Effects Following Coronary Occlusion (Rat) With IV Cordarone

|  | VPC/30 min | VT Events | VF Events |
|---|---|---|---|
| Saline (no amiodarone) | 226 ± 96 | 17 ± 9 | 5 ± 5 |
| 0.5 mg/kg (n = 5) | 222 ± 30 | 17 ± 5 | 2 ± 1 |
| 1 mg/kg (n = 5) | 145 ± 29 | 15 ± 30 | 0.6 ± 2 |
| 3 mg/kg (n = 5) | 82 ± 45 | 5 ± 6 | 0.3 ± 0 |
| 5.0 mg/kg (n = 5) | 208 ± 121 | 4 ± 5 | 0 |
| 10.0 mg/kg (n = 5) | 129 ± 135 | 3 ± 5 | 0 |
| 20.0 mg/kg (n = 5) | 200 ± 100 | 1 ± 3 | 0 |

TABLE 3

Antiarrhythmic Effects Following Coronary Occlusion (Rat) With Amiodarone-NNDMA Buffer Preparation of Example 1

|  | VPC/30 min | VT Events | VF Events |
|---|---|---|---|
| 0.5 mg/kg (n = 5) | 50 ± 5 | 6 ± 1 | 1 |
| 10.0 mg/kg (n = 5) | 31 ± 12 | 4 ± 3 | 0 |
| 20.0 mg/kg (n = 5) | 18 ± 10 | 0 | 0 |

The Antiarrhythmic action of amiodarone is primarily through its action on the potassium channel $IK_r$. The $IK_r$ channel is the conduit for rapid rectifier current that cases repolarization of myocardial cells. $IK_r$ is mediated through HERG channels that can be expressed on the surface of frogs eggs, *Xenopus Oocytes* by injecting cDNA construct into the eggs. A two microelectrode recording electrode technique can measure the potassium current through the HERG channels and the effect of amiodarone on the current. As amiodarone concentration increases the potassium current is well known to decrease in a dose dependent fashion. Amiodarone in Tween 80 and benzyl alcohol was contrasted to the effects of amiodarone in NNDMA at the same concentration, across a wide concentration range. As can be seen in FIG. 2, the concentration of amiodarone effects HERG current to a similar degree across all concentrations studied. These observations strongly support the concept that the antiarrhythmic activity of the two preparations (NNDMA and acetate buffer) are identical on a mg/ml concentration basis.

Example 4

Preparation of an Intravenous Dosage Form

A solution prepared according to Example 1 is sterilized, sealed using a sterile ultrafiltration membrane, and packaged into a sterile glass ampule and sealed under aseptic conditions giving a dosage form suitable for intravenous injection and containing about 25-100 mg/ml of amiodarone.

TABLE 1

The Solubility of Amiodarone in Different Solvents

| No | NNDMA/ml | Total ml | Solvent(s) | Final Concentration of Amiodarone (mg/ml) | pH | Stability Studies 1 week | | 2 weeks | | 4 weeks | |
|---|---|---|---|---|---|---|---|---|---|---|---|
| | | | | | | RT | 40 | RT | 40 | RT | 40 |
| 1 | 0.1 | 10 | 5% dextrose | 20 | 5.5-6.5 | clear | clear | clear | clear | clear | clear |
| 2 | 0.1 | 10 | Glycerol | " | " | " | clear | clear | Turbid | PT | PT |
| 3 | 0.1 | 10 | Glycerol, Tween 20 (9:1) | " | " | " | PT | PT | PT | PT | PT |
| 4 | 0.1 | 10 | Glycerol, Tween 40 (9:1) | " | " | " | PT | PT | PT | PT | PT |
| 5 | 0.1 | 10 | Glycerol, Tween 60 (9:1) | " | " | " | PT | PT | PT | PT | PT |
| 6 | 0.1 | 10 | Glycerol, Tween 80 (9:1) | " | " | " | PT | PT | PT | PT | PT |
| 7 | 0.1 | 10 | Glycerol, DMSO (9:1) | " | " | " | PT | PT | PT | PT | PT |
| 8 | 0.1 | 10 | 1 Propanol | " | " | " | PT | PT | PT | PT | PT |
| 9 | 0.1 | 10 | 1,2 Propanediol | " | " | " | PT | PT | PT | PT | PT |
| 10 | 0.1 | 10 | Polyethyleneglycol MW 300 | " | " | " | PT | PT | PT | PT | PT |
| 11 | 0.1 | 10 | Polyethyleneglycol MW 400 | " | " | " | PT | PT | PT | PT | PT |
| 12 | 0.1 | 10 | Polyethyleneglycol MW 600 | " | " | " | PT | PT | PT | PT | PT |

* Precipitate (PT)

What is claimed is:

1. A solution suitable for parenteral administration which comprises as an active ingredient about 10 to 100 mg/mL of amiodarone, about 1-50% by volume in NNDMA (N,N-dimethylacetamide), and the remainder being 5% dextrose solution.

2. The solution of claim 1, wherein the solution has a pH of 4.5 to 7.0.

3. The solution of claim 2, wherein the pH is from 6.0 to 6.5.

4. The solution of claim 2, wherein the pH is from 4.5 to 6.5.

5. The solution of claim 1, wherein 20 mg/mL of amiodarone is present.

6. The solution of claim 1, wherein 10-100 mg/mL of amiodarone is present in about 1% by volume in NNDMA and the remainder being 5% dextrose solution.

7. The solution of claim 6, wherein the pH is from 4.5 to 6.5.

8. The solution of claim 7, wherein the pH is from 6.0 to 6.5.

9. The solution of claim 1, wherein 10-20 mg/mL of amiodarone is present.

10. The solution of claim 1, wherein 10-20 mg/mL of amiodarone is present in about 1% by volume in NNDMA and the remainder being 5% dextrose solution.

11. The solution of claim 10, wherein the pH is from 4.5 to 6.5.

12. The solution of claim 11, wherein the pH is from 6.0 to 6.5.

13. The solution of claim 1, wherein 2% by volume of NNDMA is present.

14. The solution of claim 13, wherein the pH is from 4.5 to 6.5.

15. The solution of claim 13, wherein the pH is from 6.0 to 6.5.

16. The solution of claim 1, wherein 10-20 mg/mL of amiodarone is present in about 2% by volume in NNDMA and the remainder being 5% dextrose solution.

17. The solution of claim 16, wherein the pH is from 4.5 to 6.5.

18. The solution of claim 17, wherein the pH is from 6.0 to 6.5.

* * * * *